United States Patent [19]

Volodina et al.

[11] Patent Number: 5,474,600
[45] Date of Patent: Dec. 12, 1995

[54] APPARATUS FOR BIOLOGICAL PURIFICATION AND FILTRATION OF AIR

[76] Inventors: Elena V. Volodina, ploschad Vosstania, 1, kv.431; Alexandr V. Nagolkin, prospekt Universitetsky, 21, korpus 1, kv.65., both of Moscow, Russian Federation

[21] Appl. No.: 182,066
[22] PCT Filed: May 12, 1993
[86] PCT No.: PCT/RU93/00107
  § 371 Date: May 13, 1994
  § 102(e) Date: May 13, 1994
[87] PCT Pub. No.: WO93/23171
  PCT Pub. Date: Nov. 25, 1993

[30] Foreign Application Priority Data

May 13, 1992 [RU] Russian Federation ........... 5048011

[51] Int. Cl.⁶ .................................................. B03C 3/011
[52] U.S. Cl. ........................ 96/57; 55/279; 96/59; 96/69; 96/97; 96/99
[58] Field of Search ............................ 96/55, 57, 59, 96/65, 69, 70, 97, 99; 95/63, 69, 70, 78; 55/DIG. 39, 279; 422/22, 120; 435/266

[56] References Cited

U.S. PATENT DOCUMENTS

| 3,735,560 | 5/1973 | Wellman | 55/481 X |
| 3,798,879 | 3/1974 | Schmidt-Burbach et al. | 55/527 X |
| 3,918,939 | 11/1975 | Hardt | 96/99 |
| 4,597,781 | 7/1986 | Spector | 96/57 X |
| 4,629,479 | 12/1986 | Cantoni | 96/55 |
| 4,955,991 | 9/1990 | Torok et al. | 96/55 X |
| 5,034,032 | 7/1991 | Yikai et al. | 96/55 |

FOREIGN PATENT DOCUMENTS

| 2220311 | 10/1974 | France. |
| 2658510 | 6/1978 | Germany. |
| 55-28736 | 7/1980 | Japan. |
| 1346207 | 10/1987 | U.S.S.R.. |

Primary Examiner—Richard L. Chiesa
Attorney, Agent, or Firm—Ladas & Parry

[57] ABSTRACT

The invention relates to apparatus for biological purification and filtration of air. The apparatus includes a coarse filter (1), an ionizer (5), an additional plate (9) and a fine filter (10), which are installed in this order along the path of the gas flow, and a power source (23). The coarse filter (1) is essentially an electrostatic precipitator consisting of three plates (2,3,4) adjacent to each other, the outer-most (2,3) of which are made of a cellular metal and are connected electrically to the opposite-in-sign terminals of the power source (23), whereas the central plate (4) is made of polyurethane foam. The coarse filter (1) abuts closely on the cylindrical nondischarge electrode (6) of the ionizer (5).

11 Claims, 3 Drawing Sheets

APPARATUS FOR BIOLOGICAL PURIFICATION AND FILTRATION OF AIR

FIELD OF THE INVENTION

The present invention relates to air purification plants and more particularly to apparatus for biological purification and filtration of air.

PRIOR ART

An apparatus for biological purification of air is known from U.S. Pat. No. 3,918,939, said apparatus comprising a housing, at least one nondischarge precipitation electrode and at least one discharge electrode.

In the cited apparatus, particles suspended in air are forced to enter a working zone where they are subjected to electric forces influencing the magnitude and polarity of their charge. Depending on the magnitude of this charge, the particles precipitate on the electrodes and collecting plates so that purification of air is ensured thereby.

In that appartus, the efficiency of filtration depends on the strength of the electric field, the air flow rate and the properties of the particles, while the efficiency of the biological purification is proportional to the consumption of energy and, as a rule, is low.

A similar apparatus for purification and filtration of air is known from Su A 1,346,207, said apparatus comprising cartridges with filter elements of basaltic cardboard with water-repellent impregnation that are arranged across the flow in parallel to each other.

In this apparatus, air containing the particles to be removed is forced through plates. Therewith, those particles are mechanically captured which have geometrical dimensions exceeding the dimensions of the pores, in the cardboard.

In addition to this, the water-repellent impregnation of the cardboard results in the particles getting an electrostatic charge which causes them to precipitate on the walls of the pores. However, the cardboard used in the apparatus has low permeability and the pores are small in size this substantially increasing its aerodynamic drag, this limiting the service life. As a result, this apparatus has a short service life since the pores get rapidly clogged up with the particles captured thereby, and the water-repellent impregnation loses its tribostatic properties with time. Besides, it is necessary that a substantial positive pressure be built up in the system to ensure the operation of such an apparatus.

An apparatus for biological purification and filtration of air is also known from Japanese Application No. 55-28736, said apparatus comprising a coarse filter, an ionizer formed by at least a pair of electrodes connected to the opposite sign terminals of a power source, and a fine filter, which are installed in this order along the path of the gas flow. The coarse filter is made of woven filtering material.

The ionizer includes oppositely charged electrodes.

The fine filter comprises successive layers of woven filtering material and a reservoir filled with liquid.

Air to be purified is fed forcibly to the apparatus and passes through the coarse filter where the particles which have a size greater than the size of the cells in the woven material are captured. The particles remaining in the air then enter the ionization zone of the ionizer together with the air flow, where they acquire an electric charge and deposit on the wonven fine filter and on the surface of the liquid.

In this apparatus, a combined mechanism for collecting the particles is realized: due to mechanical capture and electric forces, as well as molecular forces.

Since the efficiency of cleaning is determined by the quantity of captured particles it is extremely important that each of the components of the cleaning apparatus captures as many particles as possible. However, in this construction the quantity of particles captured on the plate of the coarse filter will, as in the apparatuses described above, depend on the size of the cells in the filtering material, i.e., the smaller the size of the cells, the higher the efficiency of filtration (the smaller the particles removed), but simultaneously there is an increase in aerodynamic drag, and this leads to a shorter service life since the filtering material becomes fouled more rapidly and higher air pressure is required to overcome the resistance of the filter- a factor which causes additional consumption of energy.

All the designs described above show low efficiency of biological purification of air and shorter service life; besides, their characteristics are unstable and depend on the "fouling" of filtering materials. It should also be pointed out that the ionizers of the electrostatic precipitators release large quantities of ozone and nitrogen oxides, and this makes it difficult to use them in human environment.

SUMMARY OF THE INVENTION

At the basis of this invention is the task of providing an apparatus for purification and filtration of air, the construction of which would allow it to capture most of the particles to be removed, without a significant increase in the aerodynamic drag of the filtering plates, so that the maximum number of microorganisms and viruses are inactivated thereby, the construction characterized by the low quantity of ozone egressing from the plant. This is accomplished in an apparatus for biological purification of gas, comprising a coarse filter, an ionizer formed by at least a pair of electrodes connected to the opposite-in-sign terminals of a power source and a fine filter, which are installed in this order along the path of the gas flow, in that according to the invention, use is made of a course electrostatic precipitator consisting of at least three plates arranged across the gas flow adjacent to each other, the outermost plates being made of gas-permeable current-conducting material and connected to the opposite-in-sign terminals of the power source, whereas the central plate located therebetween is made of high-porous electret material. Therewith, it is advisable to use cellular metal having open porosity of at least 85% and pore diameter of 0.3 mm to 5 mm, as such gas-permeable current-conducting material and it is advisable to use polyurethane foam having an open porosity of at least 85% and a pore diameter of 0.3 mm to 5 mm as the highporous an electret material.

It is desirable that the size of the pores in the filter elements be selected to be from 0.3 mm to 5 mm, since a reduction of the size below 0.3 mm leads to a considerable rise in aerodynamic drag, whereas an increase above 5 mm reduces the influence of electric forces on the particles, this in turn impairing the efficiency of their removal.

In the case where the ionizer comprises a discharge electrode shaped as a needle arranged along the gas flow, and a nondischarge electrode shaped essentially as a hollow cylinder arranged coaxially relative to the needle it is desirable that the end face of the cylindrical electrode abuts on the nearest current-conducting plate so that it overlaps it completely.

It is advisable that the fine filter be made similar to the coarse filter. Wherein, the plates of the fine filter can be made of metal and arranged either across the gas flow or in parallel therewith. In this case, in order to ensure minimum weight and improve the conditions for draining the charge off, it is preferable to make the current-conducting plates of the fine filter perforated.

Based on conditions of arrangement, for instance, with the housing made as a cylinder, the plates of the fine filter can also be made as coaxially arranged cylinders.

In the apparatus for purification and filtration of air it is advisable to install an additional ionizer which has a construction similar to that of the main ionizer. Wherein, the pairs of electrodes of the main and additional ionizers should be connected to the power source so that the nondischarge electrode of the first ionizer and the needle of the second ionizer are connected to the same terminal of the power source, and the needle of the first ionizer and the nondischarge electrode of the second ionizer connected to the terminal of the power source having the opposite sign.

It is also desirable to use cylinders having different internal diameters as the nondischarge electrodes in the main and additional ionizers.

It is preferable to form an ionizer from a plurality of, e.g., hexahedral prisms arranged compactly and oriented along the direction of the gas flow, said prisms having their side faces abuting on each other, thus forming a honeycomb structure. Wherein, the discharge electrodes made as needles are arranged along the axial lines of the prisms, whereas the current-conducting plate abutting on the ionizer is made of such a size that it overlaps the entire end surface of the honeycomb structure.

BRIEF DESCRIPTION OF THE DRAWINGS

Hereinafter the invention will be explained by a description of embodiments with reference to the accompanying drawings in which according to the present invention.

BEST MODE OF CARRYING OUT THE INVENTION

Figure 1:
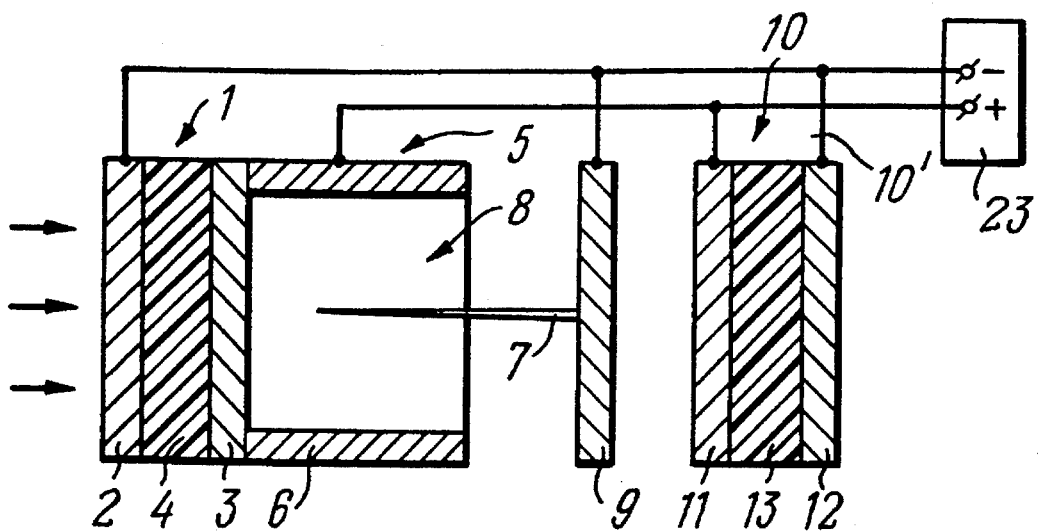
FIG. 1 shows schematically a general view of the apparatus for biological purification and filtration of air, in a longitudinal section.

With reference to FIG. 1, the apparatus for biological purification and filtration of air, according to the invention, comprises a coarse filter 1 formed by two plates 2 and 3 made of gas-permeable current-conducting material, preferably cellular metal. This material is characterized by good electric conductivity, high porosity, stable structure. A plate 4 of a dielectric, preferably made of a high-porous electret material such as, for instance, polyurethane foam is inserted between these plates 2 and 3. This material is characterized by high porosity (up to 99%), stable structure, good electric and tribostatic properties.

It is desirable that the size of the pores be selected to meet the requirements for maximum permeability and sufficiency of the electrostatic forces for precipitation of charged particles.

The current-conducting plates 2 and 3 are connected electrically to the opposite-in-sign terminals of a power source.

An ionizer 5 formed by a nondischarge electrode 6 and a discharge electrode 7 is located downstream of the last plate 3 in the path of gas flow. wherein, The nondischarge electrode 6 is made as a cylinder 6 forming an ionization chamber 8, whereas the discharge electrode is made as a needle 7 arranged along the axis of the above-mentioned cylinder 6. The end face of the cylindrical nondischarge electrode 6 abuts on the current-conducting plate 3 of the coarse filter 1 and is in electrical contact therewith.

An additional plate 9, made of current-conducting high-porous material like the plates 2 and 3 is mounted at the base of the needle 7. The plate 9 is in electrical contact with the needle 7 and is connected to the terminal of the power source which has the sign opposite to that of the plate 3.

The additional plate 9 is designed for additional filtration and electrostatic precipitation of the charged particles, as well as for restriction of the ionization zone and reduction of the quantity of ozone released.

A fine filter 10 which has a construction similar to that of the coarse filter is located downstream of the additional plate 9. The current-conducting plates 11, 12 of the fine filter 10 are also made of cellular metal having a porosity of at least 86%, whereas the dielectric plate 13 arranged between them is of polyurethane foam. The first current-conducting plate 11 in the path of the gas flow, which is the plate nearest to the additional plate 9, is connected to the terminal of the power source, which is opposite in sign to the charge of the plate 9, whereas the second current-conducting plate 12 is connected to the terminal of the power source, which has the same sign as the plate 9. Such a connection of the current-conducting plates 11 and 13 of the fine filter 10 ensures higher probability of precipitation of the charged paticles onto the plates.

Figure 2:
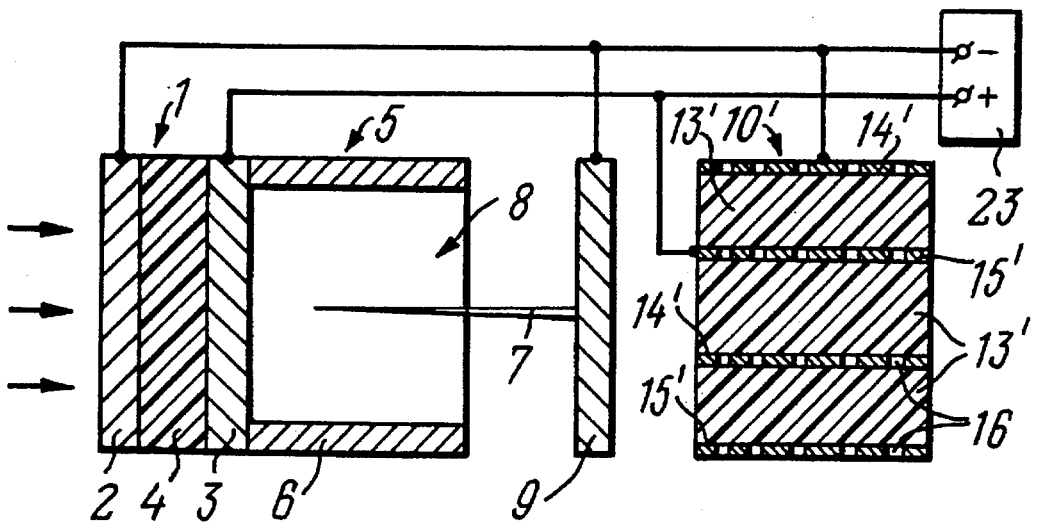
FIG. 2 is an embodiment of this apparatus with plates of the fine filter positioned in parallel in a longitudinal section.

The embodiment of the apparatus shown in FIG. 2, in contrast to the apparatus shown in FIG. 1, comprises a fine filter 10' with plates 13', 14' and 15' arranged along the path of gas flow. The current-conducting plates 14' and 15' are made of a sheet metal having perforations 16, whereas the dielectric plates 13' are made of polyurethane foam. The current-conducting plates 14' and 15' are alternately connected to the opposite-in-sign terminals of the power source. The perforations 16 of the plates 14' and 15' are desirable to enhance draining the charge off and reduce the weight of the current-conducting plates.

Figure 3:
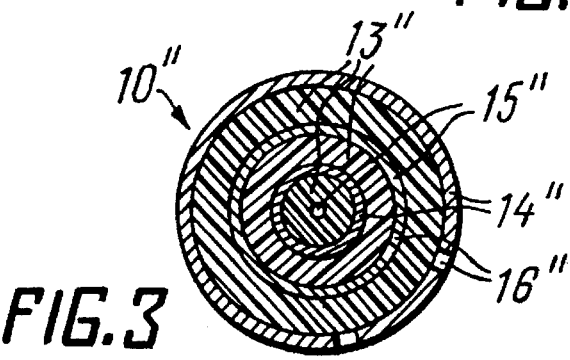
FIG. 3 is the fine filter with plates shaped as coaxial cylinders, end view, in a longitudinal section.

The fine filter 10" shown in FIG. 3 differs from the filter 10' shown in FIG. 2 in that plates 13", 14" and 15" are made as cylinders arranged coaxially relative to each other, the cylinder coincident with the axis having a zero diameter, i.e., it is essentially a rod. Such an embodiment increases the filtering surface without increasing the overall dimensions of the filter, improves the capacity of the filter as well as ensures convenient arrangement.

Figure 4:
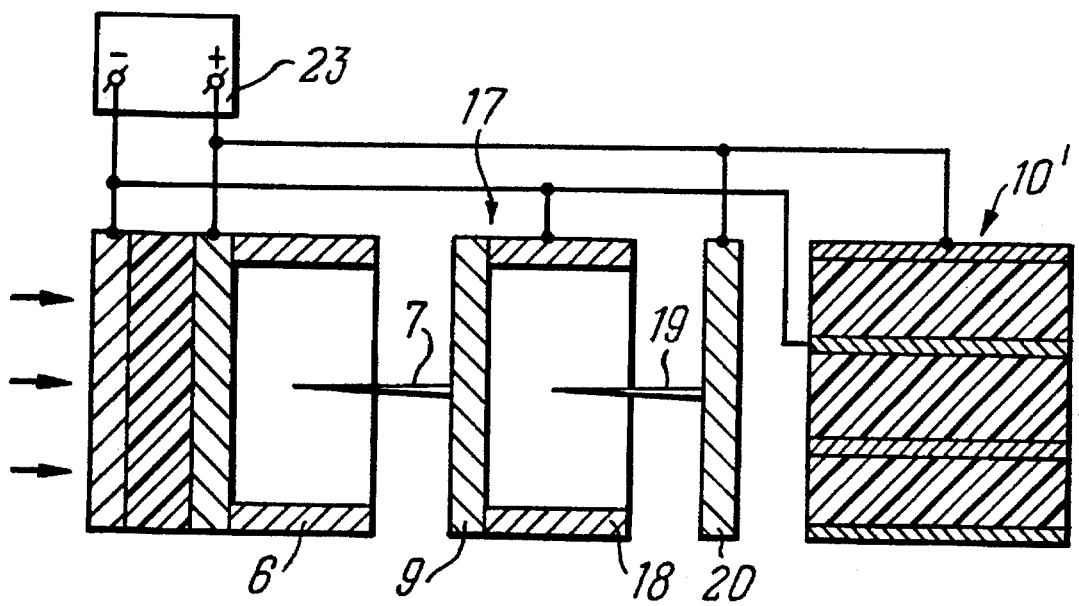
FIG. 4 is an embodiment of this apparatus with an additional ionizer, in a lateral section.

The embodiment of the apparatus shown in FIG. 4, in contrast to the embodiment shown in FIG. 1, comprises an additional ionizer 17 arranged in succession with the main ionizer. The additional ionizer 17 is located so that its cylindrical electrode has the end face thereof abutting the plate 9 and, correspondingly, it has a charge of the same sign as the plate 9. A needle 19 and a plate 20 are connected to the terminal of the power source having an opposite sign as compared with that of the charge of the cylindrical electrode 18. In this case, the air which flows through the apparatus to be purified, passes successively through the ionization chambers having corona discharges opposite to each other in sign, and this causes recharging of the particles to be removed so that the probability of inactivation of the microorganisms and viruses that are on them or suspended in the air is increased thereby and, hence, the efficiency of purification is improved.

Figure 5:
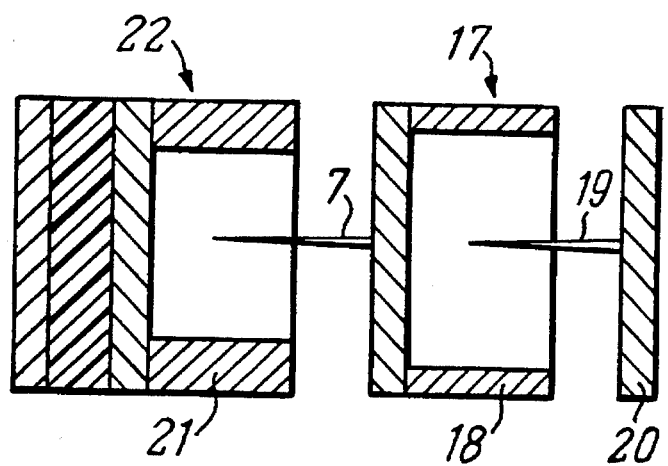
FIG. 5 is an embodiment of this apparatus in which the cylindrical electrodes of the ionizer are made with different internal diameters, in a longitudinal section.

In contrast to FIG. 4, FIG. 5 shows schematically an embodiment of cylindrical electrodes 18 and 21 which are part of ionizers 17 and 22, arranged in succession with one another and with different internal diameters. In this particular case, the internal diameter of the cylindrical electrode 21 of the ionizer 22, which is the first one in the path of flow, is smaller than the internal diameter of the cylindrical electrode 18 of the additional ionizer 17. Such an embodiment ensures optimization of the conditions for charging and recharging the particles, thus improving the efficiency of purification.

The discharge electrodes of the main ionizer 17 and the additional ionizer 22 are connected to the opposite-in-sign terminals of the power source 23.

Figure 6:
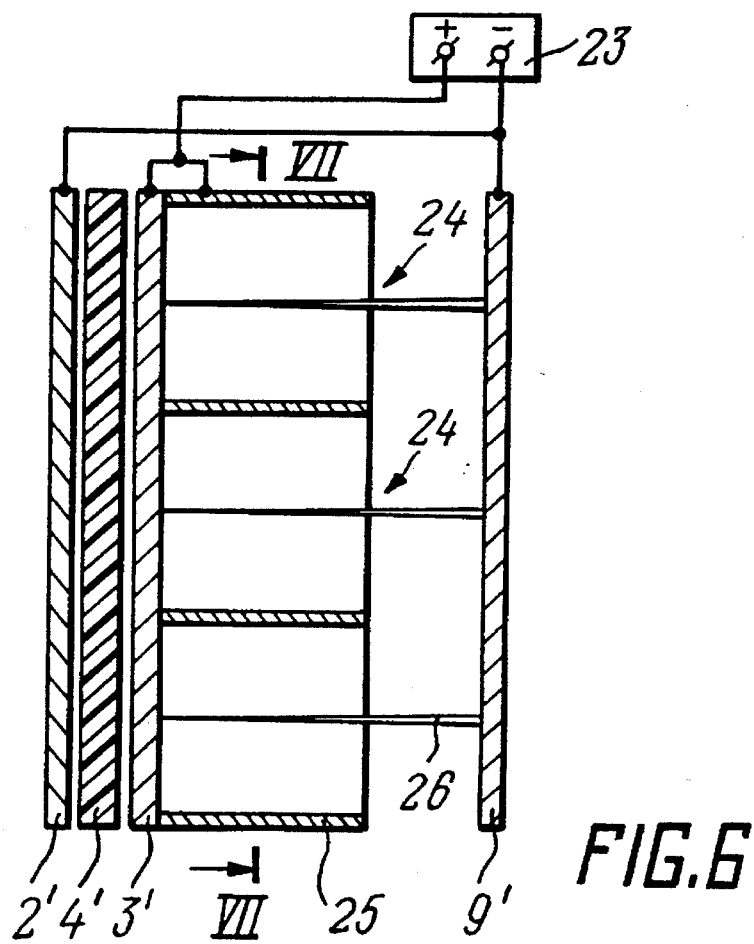
FIG. 6 shows schematically an ionizer having a plurality of electrode pairs, in a longitudinal section.
Figure 7:
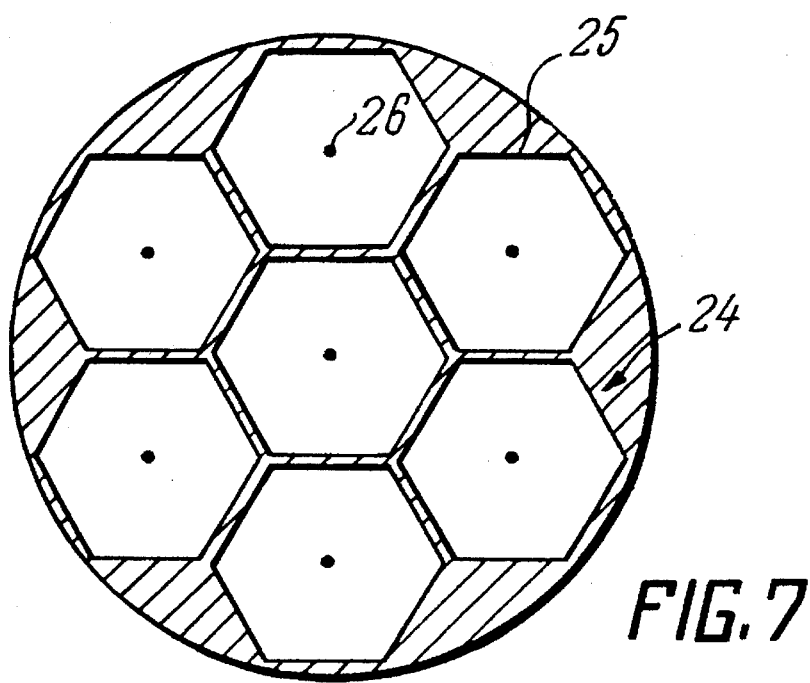
FIG. 7 is a section through UP-UP in FIG. 6.

FIGS. 6 and 7 show schematically an embodiment of an ionizer having a plurality of electrode pairs 24 forming thereby a plurality of ionization chambers. The most compact structure is obtained when nondischarge electrodes 23 are shaped as hexahedral prisms, whereas the discharge electrodes are made as needles 26, and this also substantially improves the manufacturing process. The current-conducting plate 3' of the coarse filter, which is the plate nearest to the ionizers, is made of such a size that it overlaps all the internal cavities of the prism-like electrodes 25 of the ionizer.

The apparatus illustrated in FIG. 1 operates in the following manner.

When the power source 23 is switched on, all the elements connected to its terminals acquire an electric charge. These elements include the plates 2 and 3 of the coarse filter and the plates 11 and 12 of the fine filter as well as the additional plates 9 and electrodes 6 of the ionizer. With this, every other element, or, if the elements are connected to each other, every other combination of elements is connected to the opposite-in-sign terminals of the power source so that an electric field appears between plates 2 and 3 and plates 11 and 12 of the filters, which depolarizes the plates 4 and 13 made of a dielectric, whereas a corona discharge appears between the electrodes 6 and 7 of the ionizer. The air being purified passes through the current-conducting plates 2 and 3 and the dielectric plates 4 of the coarse filter where the largest particles are restrained due to mechanical capture and the forces of electric attraction.

Since porous cellular material is used for the filtering plates in contrast to the known porous structures, for example, nets, more efficient capturing is ensured since it is determined not only by the size of the cell, in this case by the size of the pores, but also by the thickness of the filter element. The configuration of a pore passage which is, as a rule, curvilinear, does not allow the particles to fly freely therethrough without coming into contact with its surface. And such a contact will lead either to retardation or to final capture of the particles. Therewith not only those particles which have a size exceeding that of the pores will be captured as in woven structures, but also particles of a smaller size because they become entangled or are caught in irregularities of the pore passage. Particles possessing an initial charge will stay for a longer time under the influence of the charged plates 2 and 3 of the coarse filter 1 due to the mechanism of retardation described above so that the probability that they will precipitate under the effect of electric forces consequently increases.

The particles microorganisms and viruses that have passed through the coarse filter 1 enter the ionizer 5. With the plate 3 of the coarse filter 1 arranged immediately adjacent to the end face of the cylindrical electrode 6 of the ionizer 5, the most optimum distribution of the electric field inside the ionization chamber 8 is ensured so that the particles, microorganisms and viruses leaving the coarse filter immediately find themselves under its influence, and the particles acquire an additional charge, whereas the microorganisms and viruses are inactivated.

Depending on the charge acquired, the particles with the inactivated microorganisms and viruses partially precipitate on the surfaces of the electrodes 6 and 7. As known, a corona discharge is accompanied by the release of ozone which in large quantities has an unfavorable effect on human beings. The tight fit of the plate 3 against the ionization chamber 8, in the first place improves conditions for changing the particles and inactivating the microorganisms and, viruses and in the second place the ozone released in the change 8 decomposes upon contact with the plate.

Downstream of the ionizer, the air flows through the additional plate 9 which is connected to the needle 7 of the ionizer and which, since it is made of cellular metal, also captures a portion of the particles, inactivates the microorganisms and viruses. In addition to this, the additional plate 9 restricts the ionization chamber 8 to some extent at the exit side, thus improving the charging conditions and reducing the quantity of ozone released during a corona discharge. As a result, the total content of ozone in the air flow leaving the apparatus of the present invention does not exceed the adopted values for the maximum allowable concentrations.

Then, the air with the particles, microorganisms and viruses still left suspended therein enters the fine filter 10 where, as in the coarse filter, further mechanical and electrostatic precipitation of the particles, and inactivation of the microorganisms and viruses take place. The air thus purified and made harmless by removal of microorganisms and viruses therefrom flows the fine filter 10 to the outlet of the apparatus.

The apparatus shown in FIGS. 2 and 3 differs from the apparatus shown in FIG. 1 only by an alternative embodiment of the fine filter 10, 10". The air is purified therein and the microorganisms and viruses inactivated in the same manner as in the apparatus shown in FIG. 1.

The apparatus shown in FIG. 4 operates in the same manner as the apparatus shown in FIG. 1, but the air to be purified additionally passes through an additional ionizer 17 installed in succession with the main ionizer 5. The electrodes 18 and 19 of that ionizer 17 are connected to the power source 23 in such a manner that the corona discharge produced therein is opposite in sign to the corona discharge in the main ionizer 5. For this reason, the air thus being purified is additionally subjected to the influence of the charge of opposite sign, and this is favorable for additional precipitation of the particles on the electrodes 18 and 19, whereas the recharging of the microorganisms and viruses makes their inactivation more probable, i.e. they are killed in larger quantities under the influence of a field having the opposite sign.

The apparatus shown in FIG. 5 operates in the same manner as the apparatus shown in FIG. 4 but, since the cylindrical electrodes 21 and 18 having different internal diameters are used in the main ionizer 22 and in the additional ionizer 17, respectively, the possibility is ensured for creating an electric field that is optimum for capturing the particles in dependence on their size. This is because in order to capture larger particles it is necessary to have a higher electric charge which, in particular, depends on the strength of the electric field determined in turn by the distance between the discharge and nondischarge electrodes: the smaller this distance, the higher the strength of the electric field.

For the same reason, as well as to ensure safe operation from the point of view of the maximum strength of the electric field allowable in the ionization chambers, use is made of an ionizer arrangement as shown in FIG. 6 comprising a plurality of electrode pairs 24. In the apparatus shown in FIG. 6, the air to be purified flows into a plurality of ionization chambers formed by the electrode pairs 24 where the precipitation of particles and the inactivation of microorganisms and viruses take place. Then the air being purified passes through the elements of the apparatus according to the present invention in the same manner as in the embodiment shown in FIG. 1.

Thus, an apparatus made in accordance with the present invention, thanks to the use of a coarse electrostatic precipitator made on the basis of cellular metal and polyurethane foam, as well as its arrangement adjacent to an ionizer, has made it possible to eliminate the shortcomings existing in the known purification apparatuses during operation there is no substantial increase in the aerodynamic drag of the filtering plates and consequently its service life does not become shorter, there is an increase in the quantity of the inactivated microorganisms and viruses the amount of ozone released from the apparatus is substantially reduced.

A mock-up of the apparatus in accordance with FIG. 1 has been made, and its tests have been carried out with ambient air purified therein, as a result of which we have obtained the following data:
biological purification efficiency is 100%;
filtration efficiency for particles having a size from 0.01 micron to 10 microns is 99%; and
capacity is 135 m³/hour.

The apparatus is simple in operation, has small dimensions and superior to that of known apparatus.

INDUSTRIAL USABILITY

The apparatus can used in medicine for biological purification of air in operating, germ-free biological and other rooms; in pharmacology and microbiology; at locations where stringent requirements are imposed on purity and sterility of air, as well as in the electronic industry and other industries where the quality of products manufactured is dependent upon the purity of the air.

We claim:
1. An apparatus for biological purification and filtration of gas, said apparatus comprising a power source (23), a coarse filter (1), an ionizer (5) formed by at least a pair of electrodes (6, 7), with a first of said pair of electrodes connected to a first terminal of the power source (23) and a second of said pair of electrodes connected to an opposite-in-sign terminal of the power source, and a fine filter (10), said coarse filter, ionizer and fine filter being arranged in a sequence such that gas flowing along a path through the apparatus will pass through the coarse filter, ionizer and fine filter in that order, said coarse filter comprising an electrostatic precipitator having at least three plates (3, 2, 4) arranged across the path of the gas flow adjacent to each other, said at least three plates comprising first and second outermost plates (2, 3) with a central plate (4) therebetween, said first and second outermost plates being made of gas-permeable and current-conducting material, with said first and second plates being connected electrically to the first and opposite-in-sign terminals of the power source respectively, the central plate (4) located therebetween being made of high-porous electret material.

2. The apparatus according to claim 1, wherein said ionizer (5) comprises a first discharge electrode shaped as a needle (7) arranged along the path of the gas flow, and a first non-discharge electrode shaped essentially as a hollow cylinder (6) arranged coaxially relative to the needle, said cylindrical electrode having an end face which abuts said second outermost plate.

3. The apparatus according to claim 2, further comprising an additional ionizer (17) arranged in succession with the main ionizer (5), said additional ionizer comprising a second discharge electrode shaped as a needle and a second non-discharge electrode shaped as a hollow cylinder. said first and second discharge electrodes (7, 19) being connected to opposite-in-sign terminals of the power source.

4. The apparatus according to claim 3, wherein the first and second cylindrical non-discharge electrodes (18, 21) of the ionizer and additional ionizer (17, 5) have different internal diameters.

5. The apparatus according to claim 1, wherein the first and second outermost plates are made of cellular metal having an open porosity of at least 85% and a pore diameter of from 0.3 mm to 5 mm.

6. The apparatus according to claim 1, wherein the central plate is made of polyurethane foam having an open porosity of at least 85% and a pore diameter of from 0.3 mm to 5 mm.

7. The apparatus according to claim 1, wherein said fine filter (10) comprises two outer plates and an inner plate, each of said outer plates is made of a gas permeable, current conducting material and said inner plate is made of a high-porous electret material.

8. The apparatus according to claim 1, wherein the fine filter (10) comprises at least three plates (13', 14', 15') which are arranged in parallel with the path of the gas flow.

9. The apparatus according to claim 8, wherein two of the at least three plates of the fine filter (10) are current-conducting plates (14', 15') which are perforated with holes (16).

10. The apparatus according to claim 8, wherein the at least three plates (13', 14', 15') of the fine filter (10') are shaped as coaxially arranged cylinders.

11. The apparatus according to claim 1, wherein the ionizer is formed from a plurality of electrode pairs (24), with each of said electrode pairs having a discharge and non-discharge electrode, each of the non-discharge electrodes (25) of the ionizer being shaped as a hexahedral prism oriented along the path of the gas flow, each of the hexahedral prisms having an end face and also having side faces which abut on each other, thereby forming a honeycomb structure, each of the discharge electrodes (26) of the ionizer having the shape of a needle and being arranged along an axial line of one of the prisms, and wherein the second outermost plate (3) of the coarse filter abuts on the end face of each of the prisms (25) so that it overlaps them completely.

\* \* \* \* \*